United States Patent [19]

Rajagopalan et al.

[11] Patent Number: 5,709,845
[45] Date of Patent: Jan. 20, 1998

[54] TRICYCLIC FUNCTIONAL DYES FOR CONTRAST ENHANCEMENT IN OPTICAL IMAGING

[76] Inventors: Raghavan Rajagopalan, 13031 Vinson Ct., Maryland Heights, Mo. 63043; Ella Y. Fung, 1329-D Whispering Pines, St. Louis, Mo. 63146

[21] Appl. No.: 645,376

[22] Filed: May 13, 1996

[51] Int. Cl.⁶ .................... A61K 49/00; G01N 31/00; G01N 33/48
[52] U.S. Cl. .................... 424/9.6; 424/9.44; 424/9.1; 424/1.65; 540/1
[58] Field of Search ................ 424/1.11, 1.65, 424/9.1, 9.3, 9.36, 9.361, 9.4, 9.44, 9.5, 9.6; 540/1; 546/184, 249; 548/100, 400; 534/7, 10–16

[56] References Cited

U.S. PATENT DOCUMENTS 3,655,392  4/1972  Fumia, Jr. et al. ............... 96/131
3,855,210  12/1974  Keller ...................... 260/240.9

OTHER PUBLICATIONS

Elwood (1973), J. Org. Chem., vol. 38, No. 14, pp. 2425–2430.
"Dyes Containing the Phenalene Ring System. I. Synthesis of Benzothiazole—Containing Dyes".
Elwood (1973), J. Org. Chem., vol. 38, No. 14, pp. 2430–2433.
"Dyes Containing the Phenalene Ring System. II. Electronic Spectra and their Correlations with Hücke 1 Molecular Orbital Theory".

Primary Examiner—John Kight
Assistant Examiner—Dameron Jones
Attorney, Agent, or Firm—Brian K. Stierwalt; Wendell Ray Guffey

[57] ABSTRACT

This invention provides functional dyes of the general formula:

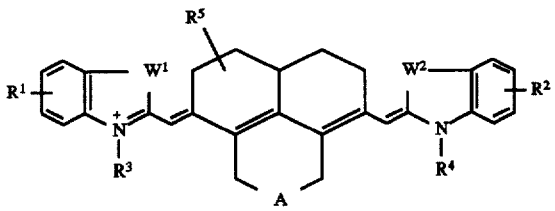

wherein $R^1$, $R^2$, and $R^5$ may be the same or different and are selected from the group consisting of hydrogen, $C_1$–$C_{10}$ alkyl, $C_1$–$C_{10}$ alkoxyl, hydroxyl, $C_1$–$C_{10}$ hydroxyalkyl, $C_1$–$C_{10}$ alkoxyalkyl, $C_1$–$C_{10}$ aryl, carboxyl, $C_1$–$C_{10}$ carboxylalkyl, halogen, nitro, $C_1$–$C_{10}$ alkoxycarbonyl, mercapto, $C_1$–$C_{10}$ mercaptoalkyl, $C_1$–$C_{10}$ alkylthio, sulfonate, and —$(CH_2)_m$—$N(R^6)(R^7)$ wherein $R^6$ and $R^7$ are independently hydrogen or $C_1$–$C_{10}$ alkyl, $C_1$–$C_{10}$ acyl, and $R^6$ and $R^7$ are capable of forming 5, 6, or 7 membered rings which may optionally be substituted with —O—, —$NR^8$, or —S—; $R^3$ and $R^4$ may be the same or different and are selected from the group consisting of $C_1$–$C_{10}$ alkyl, $C_1$–$C_{10}$ hydroxyalkyl, $C_1$–$C_{10}$ alkoxyalkyl, $C_{1–C10}$ aryl, $C_1$–$C_{10}$ carboxylalkyl, $C_1$–$C_{10}$ alkyl sulfonate, mercapto alkyl and —$(CH_2)_m N(R^6)(R^7)$; $W^1$ and $W^2$ may be the same or different and are selected from the group consisting of —S—, —O—, —Se—, —Te—, —$NR^8$ and $C(R^9)(R^{10})$; and m is about 0–10; $R^8$ is hydrogen, $C_1$–$C_{10}$ alkyl, $C_1$–$C_{10}$ alkoxy, $C_1$–$C_{10}$ mercaptoalkyl, hydroxyl, $C_1$–$C_{10}$ hydroxyalkyl, $C_1$–$C_{10}$ alkoxyalkyl, $C_1$–$C_{10}$ aryl, $C_1$–$C_{10}$ carboxylalkyl, $C_1$–$C_{10}$ alkoxycarbonyl, $C_1$–$C_{10}$ alkylthio, and —$(CH_2)_m$—$N(R^6)(R^7)$; $R^9$ and $R^{10}$ are independently hydrogen, $C_1$–$C_{10}$ alkyl, $C_1$–$C_{10}$ alkoxyl, $C_1$–$C_{10}$ hydroxyalkyl, $C_1$–$C_{10}$ alkoxyalkyl, $C_1$–$C_{10}$ carboxyalkyl, $C_1$–$C_{10}$ alkoxycarbonyl, and —$(CH_2)_m$—$N(R^6)(R^7)$; and A is selected from the group consisting of —$(CH_2)_m$, —$C(R^9)(R^{10})$, —$(CH_2)_m$—$N(R^6)(R^7)$ —O—, —S—, or —$NR^8$.

10 Claims, No Drawings

TRICYCLIC FUNCTIONAL DYES FOR CONTRAST ENHANCEMENT IN OPTICAL IMAGING

FIELD OF THE INVENTION

The invention is in the field of tomographic imaging. Particularly, the invention is in the field of optical imaging.

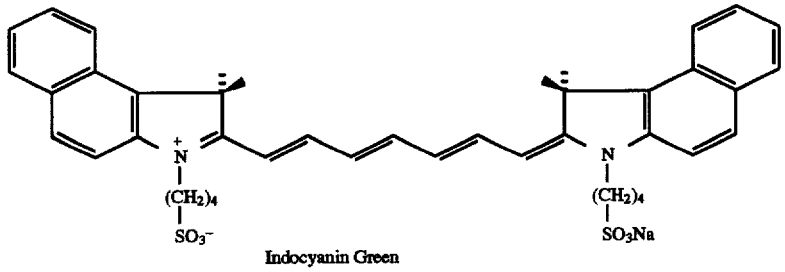

Indocyanin Green

Most particularly, the invention provides dyes for use in the field of optical imaging.

BACKGROUND OF THE INVENTION

Optical imaging with dyes permit visualization of biological activities (Blasdel, G. G.; Salama, G. *Nature* 1986, 321, 579, Grinvald, A.; Frostig, E. L.; Hildesheim, R. *Physiological Reviews* 1988, 68, 1285, Kauer, J. S. *Nature* 1988, 331, 166, Lieke, E. E.; Frostig, R. D.; Arieli, A.; Ts'o, D. Y.; Hildesheim, R. and Grinvald, A. *Annu. Rev. Physiol.* 1989, 51, 543 and reference therein). Dyes that are sensitive to physicochemical environments (such as pressure, cell membrane potential, ion concentration, acidity, partial pressure of oxygen and etc.), are subject to changes in absorption or emission of light. The resulting changes act as optical probes to transform biological activities into optical signals that can be converted into optical images.

Cyanine dyes with intense absorption and emission in the near-IR region (600–1300 nm) are particularly useful because biological tissues are optically transparent in this region. Indocyanine Green (ICG) (I) for example, with absorption maxima at around 810 nm (the isosbestic point of the hemoglobin/deoxyhemoglobin), has been used for monitoring cardiac output, hepatic function, and liver blood flow. After intravenous injection, ICG is rapidly bound by plasma proteins and remains in the blood through one circulation of heart and lungs. ICG is then taken up by hepatic parenchymal cells and secreted entirely into the bile (Osol, A.; Pratt, R. *The United States Dispensatory* Philadelphia, Toronto: J. B. Lippincott Company, 1973, 615).

Despite ICG's promising application, aqueous solutions of indocyanine green rapidly decomposes when irradiated with incandescent light. Also, ICG itself does not localize in any particular tissue.

Targeting groups can be introduced to cyanine and indocyanine dyes if essential linkers are present at a convenient site that will not interfere with the optical activity. Conventionally, these spacers have been attached at the nitrogen atom in the heterocyclic moiety. (Mujumdar, R. B.; Ernst, L. A.; Mujumdar, S. R.; Lewis, C. J.; Waggoner, A. S. *Bioconjugate Chem.* 1993, 4, 105). To effectively label targeting groups, a single spacer between the dye and the targeting group is preferred, and typically involves a multi-step synthesis (Mujumdar, R. B.; Ernst, L. A.; Mujumdar, S. R.; Lewis, C. J.; Waggoner, A. S. *Bioconjugate Chem.* 1993, 4, 105). Additional problems also arise from the photo-instability of the long olefin chain (Matsuoka, M. In *Infrared Absorbing Dyes;* Plenum: New York, 1990; Chapter 3). Cyanine dyes with shorter olefin chains are relatively stable, but their absorption and emission do not fall within the optical window (600–1300 nm) necessary for optical imaging.

There is a need to design stable dyes that possess desirable photophysical properties, stability, and targeting ability. The present invention overcomes the technical problems mentioned previously by incorporating a bifunctional spacer, and imposing rigidity on the polyene portion of the cyanine and indocyanine dyes.

SUMMARY OF THE INVENTION

This invention provides functional dyes of the general formula:

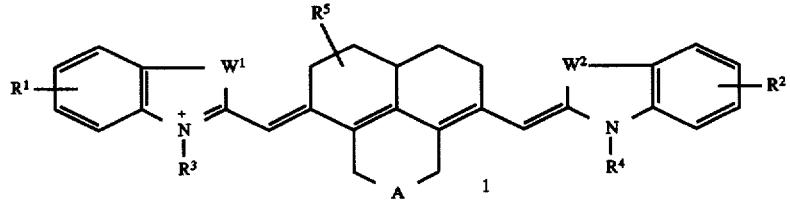

wherein R1, R2, and $R^5$ may be the same or different and are selected from the group consisting of hydrogen, $C_1$–$C_{10}$ alkyl, $C_1$–$C_{10}$ alkoxyl, hydroxyl, $C_1$–$C_{10}$ hydroxyalkyl, $C_1$–$C_{10}$-alkoxyalkyl, $C_1$–$C_{10}$ aryl, carboxyl, $C_1$–$C_{10}$ carboxylalkyl, halogen, nitro, $C_1$–$C_{10}$ alkoxycarbonyl, mercapto, $C_1$–$C_{10}$ mercaptoalkyl, $C_1$–$C_{10}$ alkylthio, sulfonate, and —$(CH_2)_m$—$N(R^6)(R^7)$ wherein $R^6$ and $R^7$ are independently hydrogen or $C_1$–$C_{10}$ alkyl, $C_1$–$C_{10}$ acyl, and $R^6$ and $R^7$ are capable of forming 5, 6, or 7 membered rings which may optionally be susbstituted with —O—, —$NR^8$, or —S—; $R^3$ and $R^4$ may be the same or different and are selected from the group consisting of $C_1$–$C_{10}$ alkyl, $C_1$–$C_{10}$ hydroxyalkyl, $C_1-C_{10}$ alkoxyalkyl, $C_1-C_{10}$ aryl, $C_1-C_{10}$ carboxylalkyl, $C_1-C_{10}$ alkyl sulfonate, mercapto alkyl and —$(CH_2)_m N(R^6)(R^7)$; $W^1$ and $W^2$ may be the same or different and are selected from the group consisting of —S—, —O—, —Se—, —Te—, —$NR^8$ and $C(R^9)(R^{10})$; and m is about 0–10; $R^8$ is hydrogen, $C_1-C_{10}$ alkyl, $C_1-C_{10}$ alkoxy, $C_1-C_{10}$ mercaptoalkyl, hydroxyl, $C_1-C_{10}$ hydroxyalkyl, $C_1-C_{10}$ alkoxyalkyl, $C_1-C_{10}$ aryl, $C_1-C_{10}$ carboxylalkyl, $C_1-C_{10}$ alkoxycarbonyl, $C_1-C_{10}$ alkylthio, and —$(CH_2)_m-N(R^6)(R^7)$; $R^9$ and $R^{10}$ are independently hydrogen, $C_1-C_{10}$ alkyl, $C_1-C_{10}$ alkoxyl, $C_1-C_{10}$ hydroxyalkyl, $C_1-C_{10}$ alkoxyalkyl, $C_1-C_{10}$ carboxyalkyl, $C_1-C_{10}$ alkoxycarbonyl; and A is selected from the group consisting of —$(CH_2)_m$—, —$C(R^9)(R^{10})$, —$(CH_2)_m$—N$(R^6)(R^7)$, —O—, —S—, or —$NR^8$. Also provided are methods of using dyes of the invention comprising administering a diagnostically effective amount of the dye to a patient and visualizing the dye.

DETAILED DESCRIPTION OF INVENTION

Cyanine dyes are symmetric molecules with two heterocyclic base groups linked by a conjugated carbon chain. These dyes absorb intensely from the visible to near-infrared (NIR) region, depending strongly on the length of the carbon chain. Bathochromic shift is often found when number of C=C unit increases (Matsuoka, M. In *Infrared Absorbing Dyes*; Plenum: New York, 1990; Chapter 2 & 3). Other structural variations that cause bathochromic shift can also be introduced into these dyes. Typically, electron donating or electron withdrawing functional groups such as alkyl, alkoxyl, alkylthio, halogen, cyano, alkoxycarbonyl, and nitro can be substituted at the appropriate electron-rich or electron deficient centers at the polyene portion of the molecule.

The cyanine dyes are generally prepared from condensation reaction between quaternary salts of heterocyclic base and bis-aldehyde or Schiff base in acetic acid/acetic anhydride (Keyes, G. H.

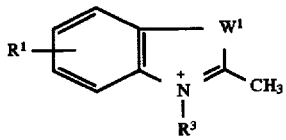

2

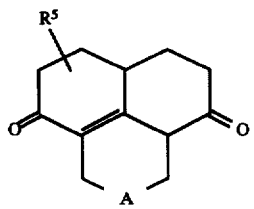

3

U.S. Pat. No. 2,251,286, 1941; Heseltine, D. W.; Brooker, L. G. S. U.S. Pat. No. 2,895,955, 1959; Reynolds, G. A.; Drexhage, K. H. *J. Org. Chem.* 1977, 42, 885). The bicyclic cyanine dyes of the present invention can be prepared by the condensation of the thiazolium (2) and the diketone (3). Asymmetric dyes with linkage groups can be prepared in a similar manner with additional synthetic steps (Mujumdar, R. B.; Ernst, L. A.; Mujumdar, S. R.; Lewis, C. J.; Waggoner, A. S. *Bioconjugate Chem.* 1993, 4, 105).

The starting materials for the bicyclic key intermediate 4 can be prepared by the well known procedures as illustrated in Schemes 1–3.

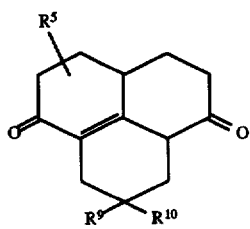

4

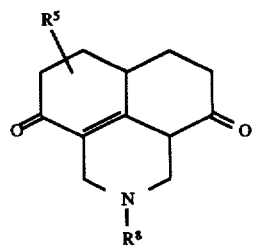

5

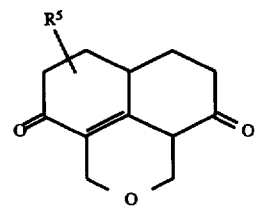

6

SCHEME 1
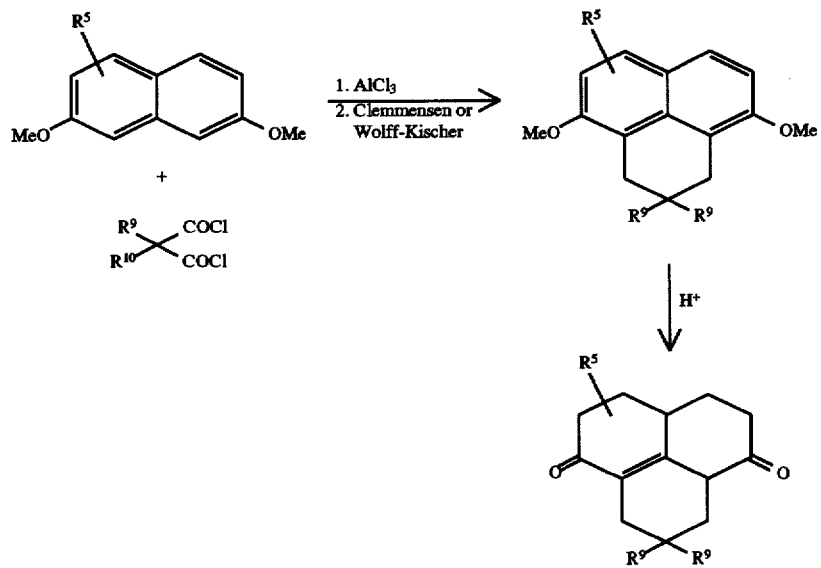
SCHEME 2
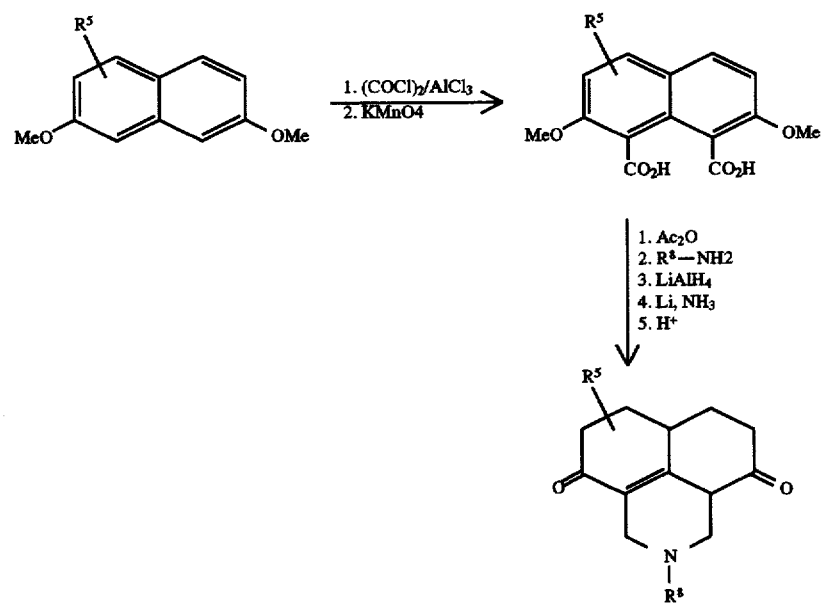

SCHEME 3

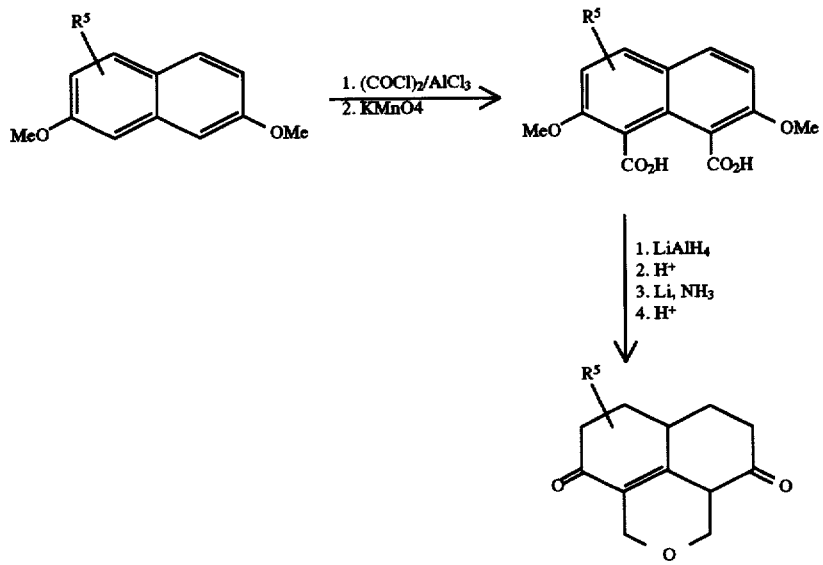

Recently, Narayanan and Patonay have demonstrated the synthesis of new cyanine dyes using 2-chloro-1-formyl-3-(hydroxymethylene) cyclohex-1-ene as a template (Narayanan, N.; Patonay, G. *J. Org. Chem.* 1995, 60, 2391). Several symmetric dyes were prepared in high yields. Like croconium dyes, the central part of these dyes contain a cyclic ring with one C=C bond and a chloride atom. Their results show that introduction of a croconic moiety into the conjugating bridge significantly shift the absorption to longer wavelengths.

The present invention describes the use of ring template strategy to synthesize stable cyanine dyes with desirable photophysical and targeting properties. Simple condensation between a quaternary salt of a heterocyclic base and the template ring will give desirable dye products that are conformationally rigid. The extended conjugated π system through this centrally located ring(s) will give intensely colored materials. With appropriate coupling groups such as acid halides, active esters, alcohols, aldehydes, amines, aryl halides, carboxylic acids, n-carboxyanhydrides, disulfides, hydrazides, iodoacetamides, isothiocyanates, imadates, maleimides, nitrenes, sulfonyl chlorides and so forth, the dye moiety can effectively label biological materials. The ring system may have at least one C=C bond. The ring system may also contain Group III, IV, V or VI elements in order to further shift the absorption maxima to longer wavelength. The ring system can also be a fused ring structure with five, six or seven membered rings. The ring structure can also be substituted with acid halides, active esters, alcohols, aldehydes, amines, aryl halides, carboxylic acids, n-carboxyanhydrides, disulfides, hydrazides, iodoacetamides, isothiocyanates, imadates, maleimides, nitrenes, sulfonyl chloride and so forth that are essential for conjugation with targeting groups (biomolecules).

Biomolecules for use with the dyes refer to all natural and synthetic molecules that play a role in biological systems. Biomolecules include hormones, amino acids, peptides, peptidomimetics, glycomimetics, vitamins, carbohydrates, proteins, deoxyribonucleic acid (DNA), ribonucleic acid (RNA), lipids, albumins, polyclonal antibodies, receptor molecules, receptor binding molecules, monoclonal antibodies and aptamers. Specific examples of biomolecules include insulins, prostaglandins, growth factors, liposomes and nucleic acid probes. Examples of synthetic polymers include polylysine, aborols, dendrimers, and cyclodextrins. The advantages of using biomolecules include enhanced tissue targeting through specificity and delivery. Coupling of the dyes to biomolecules can be accomplished by several known methods (e.g., Krejcarek and Tucker *Biochem. Biophys. Res. Comm*, 30, 581 (1977); Hnatowich, et al. *Science*, 220, 613 (1983). Typically, a nucleophilic group is reacted with an electrophilic group to form a covalent bond between the biomolecule and the dye. Examples of nucleophilic groups include amines, anilines, alcohols, phenols, thiols and hydrazines. Electrophilic group examples include halides, disulfides, epoxides, maleimides, acid chlorides, anhydrides, mixed anhydrides, activated esters, imidates, isocyanates and isothiocyanates.

Examples of suitable alkyl groups for use with the invention include methyl, ethyl, propyl, isopropyl, butyl, cyclohexyl, heptyl and octyl. Suitable alkoxyl groups include methoxyl, ethoxyl, propoxyl, butoxyl, pentoxyl, hexoxyl, heptoxyl and octoxyl. Hydroxyalkyl groups suitable for use with the invention include both mono and poly hydroxyalkyls such as hydroxyethyl, 2-hydroxypropyl, 2,3-dihydroxypropyl, 2,3,4-trihydroxybutyl, tris (hydroxymethyl) methyl and 2-hydroxy-1-hydroxymethylethyl. Suitable alkoxyalkyl groups include methoxymethyl, 2,3-dimethoxypropyl, tris (methoxymethyl) methyl, and 2-methoxy-1-methoxymethyl-ethyl. Amino groups suitable for use with the invention include aminoalkyl such as amino methyl, amino ethyl, amino propyl, hydroxyamino such as 1-amino-2,3 propandiol, 1-amino-2-ethanol, and 1-amino-3-propanol and amino acids such as alanine, aspartic acid, glycine and lysine. Carboxyalkyls include acetate, hexanoate, propionate, and butyrate. Carbohydrates, monosaccharides, and polysaccharides such as glucose, maltose, lactose and amylose. Aryl groups include phenyl and naphthyl. Alkoxycarbonyl include methyl ester, ethyl ester, propyl ester and butyl ethyl ester. Halogen groups include chlorine, fluorine, bromine and iodine. Alkylamido groups include groups such as methyl amido, ethyl amido, propyl amido and, butyl amide. Alkylthio groups include methyl thio, ethyl thio, propyl thio, and butyl thio. Aminoalkyls include $NR^6R^7$ where $R^6$ and $R^7$ can be hydrogen or $C_1$–$C_{10}$ alkyl and $R^6$ and $R^7$ are capable of forming 5, 6, or 7 membered rings which can be further substituted by a heteroatom such as O, —$NR^8$ or S, wherein $R^8$ is hydrogen, alkyl, alkoxyl, hydroxyl, hydroxyalkyl, aminoalkyl, alkoxyalkyl, alkylamido, aryl, carboxyl, carboxyalkyl, halogen, nitro, alkoxycarbonyl, mercapto, alkylthio and alkyl sulfonate.

The compositions of the invention can be formulated into diagnostic compositions for enteral or parenteral administration. These compositions contain an effective amount of the dye along with conventional pharmaceutical carriers and excipients appropriate for the type of administration contemplated. For example, parenteral formulations advantageously contain a sterile aqueous solution or suspension of dye according to this invention. Parenteral compositions may be injected directly or mixed with a large volume parenteral composition for systemic administration. Such solutions also may contain pharmaceutically acceptable buffers and, optionally, electrolytes such as sodium chloride.

Formulations for enteral administration may vary widely, as is well known in the art. In general, such formulations are liquids which include an effective amount of the dye in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement. Such doses may vary widely, depending upon the particular dye employed, the organs or tissues which are the subject of the imaging procedure, the imaging procedure, the imaging equipment being used, and the like.

The diagnostic compositions of the invention are used in the conventional manner. The compositions may be administered to a patient, typically a warm-blooded animal, either systemically or locally to the organ or tissue to be imaged, and the patient then subjected to the imaging procedure.

The following examples illustrate the specific embodiments of the invention described in this document. As would be apparent to skilled artisans, various changes and modifications are possible and are contemplated within the scope of the invention described.

EXAMPLES

Example I

Synthesis of Bicyclic Cyanine Dye Wherein A and B are —$CH_2$— Groups and $R^5$ is Methoxycarbonyl A mixture of compound 4 (2.2 g, 10 mmole) and 2 mL of triethylamine in 10 mL of acetonitrile is added with 1,2-dimethylbenzothiazolium iodide (3.0 g, 10.3 mmole). The reaction mixture is slowly heated to reflux for 16 hours. The final product is purified by recrystallization or chromatography.

Example II

Synthesis of Bicyclic Cyanine Dye Wherein A is —$CH_2$— Group, B is —O—, and $R^5$ is Methoxycarbonyl A mixture of Compound 5 (2.2 g, 10 mmole) and 2 mL of triethylamine in 10 mL of acetonitrile is added with 1,2-dimethylbenzothiazolium iodide (3.0 g, 10.3 mmole). The reaction mixture is slowly heated to reflux for 16 hours. The final product is purified by recrystallization or chromatography.

Example III

Synthesis of Cyanine Dye Wherein A is —$CH_2$— Group, B is —$N^8$, $R^5$ is —H, and $R^8$ is —(CH2) CO2CH3 Group A mixture of compound 6 (2.4 g, 10 mmole) and 2 mL of triethylamine in 10 mL of acetonitrile is added with 1,2-dimethylbenzothiazolium iodide (2.9 g, 10.3 mmole). The reaction mixture is slowly heated to reflux for 16 hours. The final product is purified by recrystallization or chromatography.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A diagnostic composition comprising a compound of the formula:

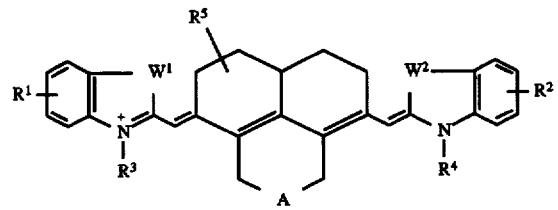

wherein $R^1$, $R^2$, and $R^5$ may be the same or different and are selected from the group consisting of hydrogen, $C_1$–$C_{10}$ alkyl, $C_1$–$C_{10}$ alkoxyl, hydroxyl, $C_1$–$C_{10}$ hydroxyalkyl, $C_1$–$C_{10}$ alkoxyalkyl, $C_1$–$C_{10}$ aryl, carboxyl, $C_1$–$C_{10}$ carboxylalkyl, halogen, nitro, $C_1$–$C_{10}$ alkoxycarbonyl, mercapto, $C_1$–$C_{10}$ mercaptoalkyl, $C_1$–$C_{10}$ alkylthio, sulfonate, and —$(CH_2)_m$—$N(R^6)(R^7)$ wherein $R^6$ and $R^7$ are independently hydrogen or $C_1$–$C_{10}$ alkyl, $C_1$–$C_{10}$ acyl, and $R^6$ and $R^7$ are capable of forming 5, 6, or 7 membered rings which may optionally be substituted with —O—, —$NR^8$, or —S—; $R^3$ and $R^4$ may be the same or different and are selected from the group consisting of $C_1$–$C_{10}$ alkyl, $C_1$–$C_{10}$ hydroxyalkyl, $C_1$–$C_{10}$ alkoxyalkyl, $C_1$–$C_{10}$ aryl, $C_1$–$C_{10}$ carboxyalkyl, $C_1$–$C_{10}$ alkyl sulfonate, mercapto alkyl and —$(CH_2)_m N(R^6)(R^7)$; $W^1$ and $W^2$ may be the same or different and are selected from the group consisting of —S—, —O—, —Se—, —Te—, —$NR^8$ and $C(R^9)(R^{10})$; and m is about 0–10; $R^8$ is hydrogen, $C_1$–$C_{10}$ alkyl, $C_1$–$C_{10}$ alkoxy, $C_1$–$C_{10}$ mercaptoalkyl, hydroxyl, $C_1$–$C_{10}$ hydroxyalkyl, $C_1$–$C_{10}$ alkoxyalkyl, $C_1$–$C_{10}$ aryl, $C_1$–$C_{10}$ carboxylalkyl, $C_1$–$C_{10}$ alkoxycarbonyl, $C_1$–$C_{10}$ alkylthio, and —$(CH_2)_m$—$N(R^6)(R^7)$; $R^9$ and $R^{10}$ are independently hydrogen, $C_1$–$C_{10}$ alkyl, $C_1$–$C_{10}$ alkoxyl, $C_1$–$C_{10}$ hydroxyalkyl, $C_1$–$C_{10}$ alkoxyalkyl, $C_1$–$C_{10}$ carboxyalkyl, $C_1$–$C_{10}$ alkoxycarbonyl, and —$(CH_2)_m$—$N(R^6)(R^7)$; and A is selected from the group consisting of —$(CH_2)_m$, —$C(R^9)(R^{10})$, —$(CH_2)_m$—$N(R^6)(R^7)$, —O—, —S—, or —$NR^8$.

2. The composition of claim 1 wherein $R^1$, $R^2$ and $R^5$ are independently hydrogen, $C_1$–$C_{10}$ alkyl, hydroxyl, $C_1$–$C_{10}$ alkoxyl, carboxyl, halogen, nitro, sulfonate, or —$(CH_2)_m$—$N(R^6)(R^7)$ wherein m is about 0–10; $R^3$ and $R^4$ are independently $C_1$–$C_{10}$ alkyl, $C_1$–$C_{10}$ hydroxyalkyl, $C_1$–$C_{10}$ carboxyalkyl, or —$(CH_2)_m$—$N(R^6)(R^7)$; $R^6$ and $R^7$ are independently hydrogen, $C_1$–$C_{10}$ alkyl, $C_1$–$C_{10}$ acyl, and hydroxyalkyl; $W^1$ and $W^2$ are independently —S— or —$C(R^9)(R^{10})$ wherein $R^9$ and $R^{10}$ are independently hydrogen, $C_1$–$C_{10}$ alkyl, $C_1$–$C_{10}$ hydroxyalkyl, $C_1$–$C_{10}$ carboxyalkyl or —$(CH_2)_m$—$N(R^6)(R^7)$; m is about 1–10; $R^8$ is hydrogen, $C_1$–$C_{10}$ alkyl, $C_1$–$C_{10}$ hydroxyalkyl, $C_1$–$C_{10}$ carboxyalkyl or —$(CH_2)_m$—$N(R^6)(R^7)$; and A may be —$(CH_2)_m$ or —$(CH_2)_m N(R^6)(R^7)$.

3. The composition of claim 2 wherein $R^1$ is hydrogen; $R^2$ is hydrogen; $R^3$ is methyl; $R^4$ is methyl; $R^5$ is methoxycarbonyl; $W^1$ is —S—; $W^2$ is —S—; and A is —$CH_2$—.

4. The composition of claim 2 wherein $R^1$ is hydrogen; $R^2$ is hydrogen; $R^3$ is methyl; $R^4$ is methyl; $R^5$ is methoxycarbonyl; $W^1$ is —S—; $W^2$ is —S—; and A is —O—.

5. The composition of claim 2 wherein $R^1$ is hydrogen; $R^2$ is hydrogen; $R^3$ is methyl; $R^4$ is methyl; $W^1$ is —S—; $W^2$ is —S—; and A is —$NR^8$, wherein —$R^8$ is carboxymethyl.

6. A method of imaging a patient comprising the administration of a diagnostically effective amount of a compound of the formula:

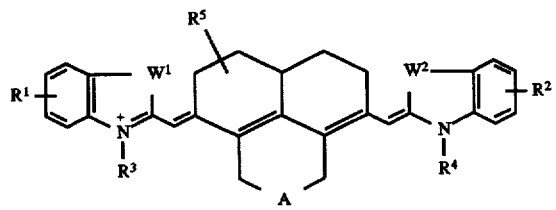

wherein $R^1$, $R^2$, and $R^5$ may be the same or different and are selected from the group consisting of hydrogen, $C_1$–$C_{10}$ alkyl, $C_1$–$C_{10}$ alkoxy, hydroxyl, $C_1$–$C_{10}$ hydroxyalkyl, $C_1$–$C_{10}$ alkoxyalkyl, $C_1$–$C_{10}$ aryl, carboxyl, $C_1$–$C_{10}$ carboxylalkyl, halogen, nitro, $C_1$–$C_{10}$ alkoxycarbonyl, mercapto, $C_1$–$C_{10}$ mercaptoalkyl, $C_1$–$C_{10}$ alkylthio, sulfonate, and —$(CH_2)_m$—$N(R^6)(R^7)$ wherein $R^6$ and $R^7$ are independently hydrogen or $C_1$–$C_{10}$ alkyl, $C_1$–$C_{10}$ acyl, and $R^6$ and $R^7$ are capable of forming 5, 6, or 7 membered rings which may optionally by substituted with —O—, —$NR^8$, or —S—; $R^3$ and $R^4$ may be the same or different and are selected from the group consisting of $C_1$–$C_{10}$ alkyl, $C_1$–$C_{10}$ hydroxyalkyl, $C_1$–$C_{10}$ alkoxyalkyl, $C_1$–$C_{10}$ aryl, $C_1$–$C_{10}$ carboxylalkyl, $C_1$–$C_{10}$ alkyl sulfonate, mercapto alkyl and —$(CH_2)_m N(R^6)(R^7)$; $W^1$ and $W^2$ may be the same or different and are selected from the group consisting of —S—, —O—, —Se—, —Te—, —$NR^8$ and $C(R^9)(R^{10})$; and m is about 0–10; $R^8$ is hydrogen, $C_1$–$C_{10}$ alkyl, $C_1$–$C_{10}$ alkoxy, $C_1$–$C_{10}$ mercaptoalkyl, hydroxyl, $C_1$–$C_{10}$ hydroxyalkyl, $C_1$–$C_{10}$ alkoxyalkyl, $C_1$–$C_{10}$ aryl, $C_1$–$C_{10}$ carboxylalkyl, $C_1$–$C_{10}$ alkoxycarbonyl, $C_1$–$C_{10}$ alkylthio, and —$(CH_2)_m$—$N(R^6)(R^7)$; $R^9$ and $R^{10}$ are independently hydrogen, $C_1$–$C_{10}$ alkyl, $C_1$–$C_{10}$ alkoxyl, $C_1$–$C_{10}$ hydroxyalkyl, $C_1$–$C_{10}$ alkoxyalkyl, $C_1$–$C_{10}$ carboxyalkyl, $C_1$–$C_{10}$ alkoxycarbonyl, and —$(CH_2)_m$—$N(R^6)(R^7)$; and A is selected from the group consisting of —$(CH_2)_m$, —$C(R^9)(R^{10})$, —$(CH_2)_m$—$N(R^6)(R^7)$, —O—, —S—, or —$NR^8$.

7. The method of claim 6 wherein $R^1$, $R^2$ and $R^5$ are independently hydrogen, $C_1$–$C_{10}$ alkyl, hydroxyl, $C_1$–$C_{10}$ alkoxyl, carboxyl, halogen, nitro, sulfonate, or —$(CH_2)_m$—$N(R^6)(R^7)$ wherein m is about 0–10; $R^3$ and $R^4$ are independently $C_1$–$C_{10}$ alkyl, $C_1$–$C_{10}$ hydroxyalkyl, $C_1$–$C_{10}$ carboxyalkyl or —$(CH_2)_m$—$N(R^6)(R^7)$; $R^6$ and $R^7$ are independently hydrogen, $C_1$–$C_{10}$ alkyl, $C_1$–$C_{10}$ acyl, and hydroxyalkyl; X is —O—, —$NR^8$ or —S—; $W^1$ and $W^2$ are independently —S— or —$C(R^9)(R^{10})$ wherein $R^9$ and $R^{10}$ are independently hydrogen, $C_1$–$C_{10}$ alkyl, $C_1$–$C_{10}$ hydroxyalkyl, $C_1$–$C_{10}$ carboxyalkyl, or —$(CH_2)_m$—$N(R^6)(R^7)$; m is about 1–10; $R^8$ is hydrogen, $C_1$–$C_{10}$ alkyl, $C_1$–$C_{10}$ hydroxyalkyl, $C_1$–$C_{10}$ carboxyalkyl, or —$(CH_2)_m$—$N(R^6)(R^7)$; and A may be —$(CH_2)_m$ or —$(CH_2)_m N(R^6)(R^7)$.

8. The method of claim 7 wherein $R^1$ is hydrogen; $R^2$ is hydrogen; $R^3$ is methyl; $R^4$ is methyl; $R^5$ is methoxycarbonyl; $W^1$ is —S—; $W^2$ is —S—; and A is —$CH_2$—.

9. The method of claim 7 wherein $R^1$ is hydrogen; $R^2$ is hydrogen; $R^3$ is methyl; $R^4$ is methyl; $R^5$ is methoxycarbonyl; $W^1$ is —S—; $W^2$ is —S—; and A is —O—.

10. The method of claim 7 wherein $R^1$ is hydrogen; $R^2$ is hydrogen; $R^3$ is methyl; $R^4$ is methyl; $W^1$ is —S—; $W^2$ is —S—; and A is —$NR^8$, wherein $R^8$ is carboxymethyl.

* * * * *